(12) United States Patent
Lord

(10) Patent No.: US 11,185,649 B2
(45) Date of Patent: *Nov. 30, 2021

(54) ELECTRONIC VAPOR PROVISION DEVICE

(71) Applicant: Nicoventures Holdings Limited, London (GB)

(72) Inventor: Christopher Lord, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/677,113

(22) Filed: Nov. 7, 2019

(65) Prior Publication Data

US 2020/0138109 A1    May 7, 2020

Related U.S. Application Data

(63) Continuation of application No. 14/401,511, filed as application No. PCT/EP2013/059954 on May 14, 2013, now Pat. No. 10,477,893.

(30) Foreign Application Priority Data

May 14, 2012 (GB) ..................................... 1208352

(51) Int. Cl.
*A24F 47/00* (2020.01)
*A61M 15/06* (2006.01)
(Continued)

(52) U.S. Cl.
CPC ............. *A61M 15/06* (2013.01); *A24F 40/40* (2020.01); *A24F 40/53* (2020.01); *A24F 40/90* (2020.01);
(Continued)

(58) Field of Classification Search
CPC ............................... A24F 40/50; A24F 47/008
See application file for complete search history.

(56) References Cited

U.S. PATENT DOCUMENTS

| 947,999 A | 2/1910 | Schweppe |
| 2,057,353 A | 10/1936 | Whittemore |

(Continued)

FOREIGN PATENT DOCUMENTS

| CA | 2641869 A1 | 5/2010 |
| CA | 2876267 A1 | 6/2015 |

(Continued)

OTHER PUBLICATIONS

Application and File History for U.S. Appl. No. 14/401,511, filed Nov. 14, 2014, Inventor: Christopher Lord, 561 pages.

(Continued)

*Primary Examiner* — Eric Yaary
(74) *Attorney, Agent, or Firm* — Patterson Thuente Pedersen, P.A.

(57) ABSTRACT

An electronic vapor provision device comprises a body and a vaporizer. The body comprises a power cell and a processor, and the vaporizer is releasably connectable to the body. The processor is configured to enter a sleep mode when the vaporizer is connected to the body and the device is inactive for an inactive time. Furthermore, the processor is configured to leave the sleep mode and enter a usable mode when the vaporizer is disconnected from the body then reconnected to the body.

13 Claims, 4 Drawing Sheets

(51) Int. Cl.
*A61M 11/04* (2006.01)
*A24F 40/90* (2020.01)
*A24F 40/40* (2020.01)
*A24F 40/53* (2020.01)
*A61M 16/00* (2006.01)
*A24F 40/10* (2020.01)

(52) U.S. Cl.
CPC ............ *A61M 11/042* (2014.02); *A24F 40/10* (2020.01); *A61M 2016/0021* (2013.01); *A61M 2016/0039* (2013.01); *A61M 2205/3653* (2013.01); *A61M 2205/8206* (2013.01)

(56) References Cited

U.S. PATENT DOCUMENTS

| | | |
|---|---|---|
| 4,947,875 A | 8/1990 | Brooks et al. |
| 5,095,921 A | 3/1992 | Losee et al. |
| 5,261,424 A | 11/1993 | Sprinkel, Jr. |
| 5,372,148 A | 12/1994 | McCafferty et al. |
| 5,808,881 A | 9/1998 | Lee |
| 5,809,997 A | 9/1998 | Wolf |
| 5,894,841 A * | 4/1999 | Voges .................. A24F 47/008 128/203.12 |
| 5,949,632 A | 9/1999 | Barreras, Sr. et al. |
| 6,040,560 A | 3/2000 | Fleischhauer et al. |
| 6,183,425 B1 | 2/2001 | Whalen et al. |
| 6,196,218 B1 | 3/2001 | Voges |
| 6,370,339 B1 | 4/2002 | Stern et al. |
| 6,873,322 B2 | 3/2005 | Hartular |
| 6,958,691 B1 | 10/2005 | Anderson et al. |
| 7,109,445 B2 | 9/2006 | Patterson et al. |
| 7,726,320 B2 | 6/2010 | Robinson et al. |
| 7,726,329 B2 | 6/2010 | Armiroli et al. |
| 8,159,204 B2 | 4/2012 | Grant |
| 8,550,069 B2 | 10/2013 | Alelov |
| 8,807,131 B1 | 8/2014 | Tunnell et al. |
| 8,997,753 B2 | 4/2015 | Li et al. |
| 9,095,175 B2 | 8/2015 | Terry et al. |
| 9,289,014 B2 | 3/2016 | Tucker et al. |
| 9,439,455 B2 | 9/2016 | Alarcon et al. |
| 9,451,791 B2 | 9/2016 | Sears et al. |
| 9,462,832 B2 | 10/2016 | Lord |
| 9,497,999 B2 | 11/2016 | Lord |
| 9,597,466 B2 | 3/2017 | Henry, Jr. et al. |
| 10,159,279 B2 | 12/2018 | Lord et al. |
| 2002/0000225 A1 | 1/2002 | Schuler et al. |
| 2003/0033055 A1 | 2/2003 | McRae et al. |
| 2003/0033067 A1 | 2/2003 | Arita et al. |
| 2003/0051181 A1 | 3/2003 | Magee et al. |
| 2003/0123328 A1 | 7/2003 | Guanter |
| 2003/0123329 A1 | 7/2003 | Guanter et al. |
| 2003/0179003 A1 | 9/2003 | Toda et al. |
| 2003/0226837 A1 | 12/2003 | Blake et al. |
| 2005/0045193 A1 | 3/2005 | Yang |
| 2005/0058441 A1 | 3/2005 | Kameyama et al. |
| 2005/0081846 A1 | 4/2005 | Barney |
| 2005/0143866 A1 | 6/2005 | McRae et al. |
| 2005/0161467 A1 | 7/2005 | Jones |
| 2005/0247305 A1 | 11/2005 | Zierenberg et al. |
| 2005/0268911 A1 | 12/2005 | Cross et al. |
| 2006/0047368 A1 | 3/2006 | Maharajh et al. |
| 2006/0090087 A1 | 4/2006 | Oh et al. |
| 2006/0100002 A1 | 5/2006 | Luebke et al. |
| 2006/0130838 A1 | 6/2006 | Lee et al. |
| 2006/0130860 A1 | 6/2006 | Cholet |
| 2006/0240798 A1 | 10/2006 | Jarosinski et al. |
| 2007/0006889 A1 | 1/2007 | Kobal et al. |
| 2007/0029969 A1 | 2/2007 | Wang et al. |
| 2007/0037610 A1 | 2/2007 | Logan |
| 2007/0045288 A1 | 3/2007 | Nelson |
| 2007/0162772 A1 | 7/2007 | Huang et al. |
| 2008/0092912 A1 | 4/2008 | Robinson et al. |
| 2008/0257367 A1 | 10/2008 | Paterno et al. |
| 2008/0272836 A1 | 11/2008 | Smit et al. |
| 2008/0276050 A1 | 11/2008 | Hsieh et al. |
| 2009/0230117 A1 | 9/2009 | Fernando et al. |
| 2009/0283103 A1 | 11/2009 | Nielsen et al. |
| 2009/0308387 A1 | 12/2009 | Andersen et al. |
| 2010/0050770 A1 | 3/2010 | Barger et al. |
| 2010/0059070 A1 | 3/2010 | Potter et al. |
| 2010/0084918 A1 | 4/2010 | Fells et al. |
| 2010/0163063 A1 * | 7/2010 | Fernando .............. H05B 1/0244 131/184.1 |
| 2010/0206306 A1 | 8/2010 | Feriani et al. |
| 2010/0242974 A1 | 9/2010 | Pan |
| 2010/0243674 A1 | 9/2010 | Furner et al. |
| 2011/0110746 A1 | 5/2011 | Smith |
| 2011/0113368 A1 | 5/2011 | Carvajal et al. |
| 2011/0210746 A1 | 9/2011 | Yugou et al. |
| 2011/0226236 A1 * | 9/2011 | Buchberger ...... A61M 15/0086 128/200.23 |
| 2011/0247620 A1 | 10/2011 | Armstrong et al. |
| 2011/0253139 A1 | 10/2011 | Guthrie et al. |
| 2011/0265806 A1 * | 11/2011 | Alarcon ................ A24F 40/485 131/273 |
| 2011/0036346 A1 | 12/2011 | Cohen et al. |
| 2011/0304282 A1 | 12/2011 | Li et al. |
| 2012/0012106 A1 | 1/2012 | Bari |
| 2012/0048266 A1 | 3/2012 | Alelov |
| 2012/0060853 A1 | 3/2012 | Robinson et al. |
| 2012/0186594 A1 | 7/2012 | Liu |
| 2012/0208601 A1 | 8/2012 | Lockwood |
| 2012/0318882 A1 | 12/2012 | Abehasera |
| 2013/0008436 A1 | 1/2013 | Von Hollen et al. |
| 2013/0042865 A1 | 2/2013 | Monsees et al. |
| 2013/0104916 A1 | 5/2013 | Bellinger et al. |
| 2013/0192615 A1 | 8/2013 | Tucker et al. |
| 2013/0199528 A1 | 8/2013 | Goodman et al. |
| 2013/0220315 A1 * | 8/2013 | Conley ................ H05B 1/0244 128/202.21 |
| 2013/0228191 A1 | 9/2013 | Newton |
| 2013/0255702 A1 | 10/2013 | Griffith, Jr. et al. |
| 2013/0269685 A1 | 10/2013 | Wachtel et al. |
| 2013/0284192 A1 | 10/2013 | Peleg et al. |
| 2013/0319439 A1 | 12/2013 | Gorelick et al. |
| 2013/0340755 A1 | 12/2013 | Ruff |
| 2013/0340775 A1 | 12/2013 | Juster et al. |
| 2014/0000603 A1 | 1/2014 | Hosemann et al. |
| 2014/0000638 A1 | 1/2014 | Sebastian et al. |
| 2014/0008384 A1 | 1/2014 | Helmlinger |
| 2014/0014126 A1 | 1/2014 | Peleg et al. |
| 2014/0060554 A1 | 3/2014 | Collett et al. |
| 2014/0096781 A1 | 4/2014 | Sears et al. |
| 2014/0123990 A1 | 5/2014 | Timmermans |
| 2014/0209105 A1 | 7/2014 | Sears et al. |
| 2014/0261414 A1 | 9/2014 | Weitzel et al. |
| 2014/0261486 A1 | 9/2014 | Potter et al. |
| 2014/0270727 A1 | 9/2014 | Ampolini et al. |
| 2014/0345635 A1 | 11/2014 | Rabinowitz et al. |
| 2014/0366894 A1 | 12/2014 | Liu |
| 2014/0366898 A1 | 12/2014 | Monsees et al. |
| 2015/0047656 A1 | 2/2015 | Robinson et al. |
| 2015/0097513 A1 | 4/2015 | Liberti et al. |
| 2015/0114408 A1 | 4/2015 | Lord |
| 2015/0128965 A1 | 5/2015 | Lord |
| 2015/0128966 A1 | 5/2015 | Lord |
| 2015/0136153 A1 | 5/2015 | Lord |
| 2015/0174348 A1 | 6/2015 | Tunnell et al. |
| 2015/0237917 A1 | 8/2015 | Lord |
| 2015/0245660 A1 | 9/2015 | Lord |
| 2015/0257448 A1 | 9/2015 | Lord |
| 2015/0336689 A1 | 11/2015 | Brown et al. |
| 2016/0206000 A1 | 7/2016 | Lord et al. |
| 2016/0242466 A1 | 8/2016 | Lord et al. |
| 2018/0153223 A1 | 6/2018 | Lord |
| 2019/0133192 A1 | 5/2019 | Lord et al. |

FOREIGN PATENT DOCUMENTS

| | | |
|---|---|---|
| CN | 1224322 A | 7/1999 |
| CN | 1280661 A | 1/2001 |
| CN | 1330427 A | 1/2002 |

(56) References Cited

FOREIGN PATENT DOCUMENTS

| | | |
|---|---|---|
| CN | 200983833 Y | 12/2007 |
| CN | 201029436 Y | 3/2008 |
| CN | 201061262 Y | 5/2008 |
| CN | 201104488 Y | 8/2008 |
| CN | 201188352 Y | 1/2009 |
| CN | 201238610 Y | 5/2009 |
| CN | 101518361 A | 9/2009 |
| CN | 201312137 Y | 9/2009 |
| CN | 101557728 A | 10/2009 |
| CN | 100566769 C | 12/2009 |
| CN | 201379072 Y | 1/2010 |
| CN | 201393548 Y | 2/2010 |
| CN | 101813963 A | 8/2010 |
| CN | 101970020 A | 2/2011 |
| CN | 201821914 U | 5/2011 |
| CN | 201830899 U | 5/2011 |
| CN | 102247640 A | 11/2011 |
| CN | 102350061 A | 2/2012 |
| CN | 102375525 A | 3/2012 |
| CN | 102934843 A | 2/2013 |
| CN | 102970885 A | 3/2013 |
| CN | 202890466 U | 4/2013 |
| CN | 203070141 U | 7/2013 |
| CN | 103237468 A | 8/2013 |
| CN | 103415222 A | 11/2013 |
| CN | 104049550 A | 9/2014 |
| CN | 203841114 U | 9/2014 |
| CN | 203986103 U | 12/2014 |
| CN | 104540406 A | 4/2015 |
| CN | 204335831 U | 5/2015 |
| DE | 102009029768 A1 | 1/2011 |
| EA | 019736 B1 | 5/2014 |
| EP | 0628336 A1 | 12/1994 |
| EP | 0701195 A1 | 3/1996 |
| EP | 0874302 A1 | 10/1998 |
| EP | 0924593 A2 | 6/1999 |
| EP | 1036289 A1 | 9/2000 |
| EP | 1494407 A1 | 1/2005 |
| EP | 1565015 A2 | 8/2005 |
| EP | 1712178 A2 | 10/2006 |
| EP | 2143346 A1 | 1/2010 |
| EP | 2292108 A1 | 3/2011 |
| EP | 2404515 A1 | 1/2012 |
| EP | 2460423 A1 | 6/2012 |
| EP | 2727619 A2 | 5/2014 |
| EP | 2908675 A1 | 8/2015 |
| EP | 3116334 A1 | 1/2017 |
| EP | 3154382 A1 | 4/2017 |
| EP | 3307097 A1 | 4/2018 |
| EP | 2908675 B1 | 1/2019 |
| EP | 3316711 B1 | 5/2019 |
| ES | 1091555 U | 10/2013 |
| GB | 2468932 A | 9/2010 |
| GB | 2502053 A | 11/2013 |
| GB | 2502055 A | 11/2013 |
| GB | 2502162 A | 11/2013 |
| GB | 2502163 A | 11/2013 |
| GB | 2502164 A | 11/2013 |
| GB | 2507103 A | 4/2014 |
| GB | 2514767 A | 12/2014 |
| JP | H05212100 A | 8/1993 |
| JP | H08511966 A | 12/1996 |
| JP | 3392138 B2 | 3/2003 |
| JP | 2006018057 A | 1/2006 |
| JP | 2006507499 A | 3/2006 |
| JP | 2006338178 A | 12/2006 |
| JP | 2009022752 A | 2/2009 |
| JP | 3159830 U | 6/2010 |
| JP | 2014504886 A | 2/2014 |
| JP | 2014534814 A | 12/2014 |
| JP | 2015512262 A | 4/2015 |
| KR | 100495099 B1 | 11/2005 |
| KR | 20110002227 U | 3/2011 |
| KR | 20110132290 A | 12/2011 |
| KR | 20120093046 A | 8/2012 |
| KR | 101256914 B1 | 4/2013 |
| RU | 72821 U1 | 5/2008 |
| RU | 2336001 C2 | 10/2008 |
| RU | 2336002 C2 | 10/2008 |
| RU | 94815 U1 | 6/2010 |
| RU | 2425608 C2 | 8/2011 |
| RU | 110608 U1 | 11/2011 |
| RU | 124120 U1 | 1/2013 |
| RU | 2509516 C2 | 3/2014 |
| SE | 9900703 L | 12/1999 |
| TW | 200928407 A | 7/2009 |
| UA | 92474 C2 | 11/2010 |
| UA | 67598 U | 2/2012 |
| UA | 100068 C2 | 11/2012 |
| UA | 100734 C2 | 1/2013 |
| UA | 78167 U | 3/2013 |
| UA | 102423 C2 | 7/2013 |
| WO | WO-9118860 A1 | 12/1991 |
| WO | WO-9418860 A1 | 9/1994 |
| WO | WO-9501137 A1 | 1/1995 |
| WO | WO-9520805 A1 | 8/1995 |
| WO | WO-9810603 A2 | 3/1998 |
| WO | WO-9817130 A1 | 4/1998 |
| WO | WO-9817131 A1 | 4/1998 |
| WO | WO-0064517 A1 | 11/2000 |
| WO | WO-2004080216 A1 | 9/2004 |
| WO | WO-2004095955 A1 | 11/2004 |
| WO | WO-2005060358 A2 | 7/2005 |
| WO | WO-2008014120 A2 | 1/2008 |
| WO | WO-2008139411 A2 | 11/2008 |
| WO | WO-2008142015 A2 | 11/2008 |
| WO | WO-2009045198 A1 | 4/2009 |
| WO | WO-2009063814 A1 | 5/2009 |
| WO | WO-2009118085 A1 | 10/2009 |
| WO | WO-2009146484 A1 | 12/2009 |
| WO | WO-2010073122 A1 | 7/2010 |
| WO | WO-2010091593 A1 | 8/2010 |
| WO | WO-2010118644 A1 | 10/2010 |
| WO | WO-2010145805 A1 | 12/2010 |
| WO | WO-2011079932 A1 | 7/2011 |
| WO | WO-2011137453 A2 | 11/2011 |
| WO | WO-2011147699 A1 | 12/2011 |
| WO | WO-2012048266 A1 | 4/2012 |
| WO | WO-2012109371 A2 | 8/2012 |
| WO | WO-2012117376 A1 | 9/2012 |
| WO | WO-2012120487 A2 | 9/2012 |
| WO | WO-2013060781 A1 | 5/2013 |
| WO | WO-2013060784 A2 | 5/2013 |
| WO | WO-2013060874 A1 | 5/2013 |
| WO | WO-2013098397 A2 | 7/2013 |
| WO | WO-2013098398 A2 | 7/2013 |
| WO | WO-2013116572 A1 | 8/2013 |
| WO | WO-2013138384 A2 | 9/2013 |
| WO | WO-2013148810 A1 | 10/2013 |
| WO | WO-2014004437 A1 | 1/2014 |
| WO | WO-2014037794 A2 | 3/2014 |
| WO | WO-2014054035 A1 | 4/2014 |
| WO | WO-2014060268 A1 | 4/2014 |
| WO | WO-2015052513 A2 | 4/2015 |
| WO | WO-2015138589 A1 | 9/2015 |
| WO | WO-2015192084 A1 | 12/2015 |
| WO | WO-2016009202 A1 | 1/2016 |
| WO | WO-2016198266 A1 | 12/2016 |
| WO | WO-2017001817 A1 | 1/2017 |

OTHER PUBLICATIONS

Application and File History for U.S. Appl. No. 14/432,752, filed Mar. 31, 2015, Inventor: Christopher Lord, 387 pages.

Application and File History for U.S. Appl. No. 15/027,344, filed Apr. 5, 2016, 535 pages, Inventors: Lord et al.

Application and File History for U.S. Appl. No. 15/231,359, filed Aug. 8, 2016, Inventor: Christopher Lord, 572 pages.

Application and File History for U.S. Appl. No. 16/188,862, filed Nov. 13, 2018, 444 pages, Inventor: Lord et al.

Application and File History for U.S. Appl. No. 15/739,019, filed Dec. 21, 2017, Inventor, Dickens, 525 pages.

(56) References Cited

OTHER PUBLICATIONS

European Patent Office Communication for Application No. EP16729349.7, dated Feb. 12, 2020, 53 pages.
Examination Report dated Feb. 3, 2020 for European Application No. 18207065.6, 5 pages.
Examination Report No. 1 dated May 2, 2016 for New Zealand Application No. 717778, 4 pages.
Extended European Search Report for European Application No. 18159788, dated Jul. 9, 2018, 8 pgs.
Extended European Search Report for Application No. 18207065, dated Apr. 12, 2019, 8 pages.
Extended European Search Report for Application No. 19164915.1, dated Jul. 8, 2019, 8 pages.
Extended Report for European Application No. 13779773.4, dated Jun. 20, 2016, 2 pages.
Extended Report dated Aug. 15, 2016 for New Zealand Application No. 71778, 3 pages.
Extended Report dated Nov. 16, 2016 for New Zealand Application No. 717778, 1 page.
Farsalinos, Konstantinos et al., "Evaluation of Electronic Cigarette Use (Vaping) Topography and Estimation of Liquid Consumption: Implications for Research Protocol Standards Definition and for Public Health Authorities Regulation" Int J Environ. Res. Public Health, 2013, 15 pages.
First Examination Report for Australian Application No. 2013261801, dated Jul. 10, 2015, 2 pages.
First Extended Report for Australian Application No. 2013331849, dated Dec. 1, 2015, 3 pages.
First Extended Report for Australian Application No. 2014333571, dated Nov. 25, 2016, 4 pages.
First Office Action for Chinese Application No. 201380054442.8 dated Aug. 30, 2016, 4 pages.
International Preliminary Report on Patentability for Application No. PCT/GB2014/053017, dated Dec. 10, 2015, 19 pages.
International Preliminary Report on Patentability for Application No. PCT/GB2016/051729, dated Sep. 20, 2017, 11 pages.
International Preliminary Report on Patentability for International Application No. PCT/EP2013/071070, dated Jun. 19, 2015, 13 pages.
International Search Report and Written Opinion for Application No. PCT/GB2016/051729, dated Aug. 22, 2016, 20 pages.
Japanese Office Action, Application No. 2018-033546, dated Oct. 29, 2019, 14 pages.
Notice of Opposition for European Application No. 14784354.4, dated Feb. 20, 2020, 43 pages.
Notice of Opposition for European Application No. 14784354.4, dated Feb. 20, 2020, 69 pages.
Notice of Opposition dated Oct. 8, 2019 for European Application No. EP13779773.4, 7 pages.
Notice of Reasons for Refusal for Japanese Application No. 2016520611, dated May 2, 2017,12 pages (with English translation).
Notice to File a Response dated Oct. 19, 2016 for Korean Application No. 10-2015-7010072, 12 pages.
Office Action and Search Report dated Sep. 29, 2019 for Chinese Application No. 201680038584.9, 17 pages.
Office Action for Canadian Application No. 2,872,764, dated Aug. 31, 2016, 6 pages.
Office Action for Canadian Application No. 2,872,764, dated Oct. 5, 2015, 6 pages.
Office Action for Canadian Application No. 2,886,922, dated Mar. 4, 2016, 3 pages.
Office Action for Canadian Application No. 2,922,280, dated Jan. 20, 2017, 4 pages.
Office Action for Canadian Application No. 2,997,062, dated Mar. 4, 2019, 6 pages.
Office Action for Chinese Application No. 201380025370.4, dated Oct. 11, 2016, 3 pages (8 pages with translation).
Office Action for Chinese Application No. 201380054442.8, dated Jun. 28, 2017, 8 pages (20 pages with translation).
Office Action for Japanese Application No. 2015-537196, dated Mar. 22, 2016, 3 Pages (7 pages with translation).
Office Action dated Mar. 21, 2016, for Chinese Application No. 201380025370.4, 23 pages.
Office Action dated Nov. 17, 2017 for Chinese Application No. 201480055728.2, 8 pages (20 pages with translation).
Office Action for Japanese Application No. 2015-537196, dated Nov. 22, 2016, 4 pages (9 pages with translation).
Office Action dated Aug. 11, 2020 for Japanese Application No. 2019112583, 6 pages.
Office Action for Japanese Application No. 2017-153826, dated Jun. 19, 2018, 3 pages (6 pages with translation).
Office Action for Japanese Application No. 2018-033546, dated Feb. 15, 2019, 5 pages (12 pages with translation).
Office Action dated Jun. 17, 2020 for Russian Application No. RU201603517, 10 pages.
Office Action dated Oct. 17, 2019 for Korean Application No. 10-2018-7038106, 17 pages.
Office Action dated Apr. 27, 2018 for Korean Application No. 2018-028946712, 19 pages.
Office Action dated Aug. 11, 2016, for Korean Application No. 10-2014-7035205, 11 pages.
Office Action dated Oct. 24, 2019 for Japanese Application No. 2018-033546,14 pages.
Office Action dated May 9, 2017 for Japanese Application No. 2016-520611, 13 pages.
Office Action dated Dec. 28, 2018 for Korean Application No. 10-2018-7014831, 8 pages (15 pages with translation).
Office Action dated Jul. 26, 2017, for Korean Application No. 10-2016-7009422,9 pages (with translation 17 pages).
Office Action dated Apr. 27, 2018 for Korean Application No. 20157010072,10 pages (19 pages with translation).
Office Action dated dated Aug. 7, 2017 for European Application No. 13779773, 2 pages.
Office Action dated Sep. 23, 2016, for Korean Application No. 10-2014-7035201, 12 pages.
Ortman, Terry, Pro Vari Menu Tour, YouTube, Mar. 9, 2011, as available at https://www.youtube.com/watch?v=IPKQOgQ42z8, as retrieved on Feb. 18, 2020, 17 pages (with machine-generated transcript).
ProVari Owner's Manual published by ProVape Copyright marking, 2010, available on web.archive.org (Dec. 16, 2011), 16 pages.
Sadaphal et al., "Random and Preiodic Sleep Schedules for Target Detection in Sensor Networks", Tata Research Development and Design Centre and Department of Computer Science and Engineering-Indlan institute of Technology, Mar. 17, 2008, 12 pages.
Screen capture of ProVari V2 information page on. the ProVape website as it appeared on May 8, 2012 via a query on web.archive. org, 10 pages.
Search Report dated Nov. 30, 2015 for Great Britain Application No. GB1511566.0, 4 pages.
Search Report dated Mar. 27, 2018 for Russian Application No. 2016147728, 3 pages (6 pages with translation).
Search Report dated Mar. 28, 2017 for Japanese Application No. 2016-520611, 18 pages (with translation 46 pages).
Second Examination Report for Australian Application No. 2013261801, dated Jun. 23, 2016, 3 pages.
Second Extended Report for Australian Application No. 2013331849, dated Feb. 5, 2016, 3 pages.
Second Extended Report for Australian Application No. 2014333571, dated Jan. 23, 2017, 4 pages.
Third Extended Report for Australian Application No. 2014333571, dated May 23, 2017, 4 pages.
Transactions of the Royal Society of Edinburgh, 1848, vol. XVIII, containing the Makerstoun Magnetical and Meteorological Observations for 1844, Robert Grant & Sons, pp. 419-424.
Williams Monique et al., "Variability Among Electronic Cigarettes in the Pressure Drop, Airflow Rate, and Aerosol Production" Nicotine & Tobacco Research Advance Access, Oct. 12, 2011, 8 pages.
Written Opinion for Application No. PCT/EP2013/059954, dated Apr. 16, 2014, 5 pages.

(56) References Cited

OTHER PUBLICATIONS

You Tube video "ProVari Menu Tour" published on Mar. 10, 2011, 18 pages.
Youtube Video "A PBusardo Review—The Provari V2—Provape" published on Feb. 28, 2012, 1 page.
Youtube, "Vlog" "Tips & Tutorial for Using Your ProVape Electronic Cigarette" by Phil fars published on Jun. 30, 2012, 5 pages.
Cambridge dictionary online, "Dictionary definition for Tap", Jan. 27, 2020, 16 pages.
Decision of Grant dated Feb. 16, 2016 for Russian Application No. 2014150496, 7 pages.
Decision to Grant dated Apr. 29, 2016 for Russian Application No. 122987, 12 pages.
International Preliminary Report on Patentability for Application No. PCT/EP2013/059954, dated Jul. 10, 2014, 6 pages.
International Preliminary Report on Patentability for Application No. PCT/EP2013/071070, dated Nov. 21, 2014, 6 pages.
International Preliminary Report on Patentability for PCT/GB2014/053027 dated Dec. 10, 2015, 19 pages.
International Search Report and Written Opinion for Application No. PCT/EP2013/059954, dated Sep. 25, 2013, 8 pages.
International Search Report and Written Opinion for Application No. PCT/EP2013/071070, dated Apr. 2, 2014, 6 pages.
International Search Report and Written Opinion of the International Searching Authority for PCT/GB2014/053027, dated Apr. 22, 2015, 13 pages.
"Load Detecting Power Supply," National Semiconductor RD-1066 Production Applications Design Center, Dec. 2008, 17 pages.
Notice of Allowance for Japanese Application No. 2015-512037, dated Dec. 15, 2015, 5 pages.
Notice of Issuance dated Jun. 16, 2021 for Chinese Application No. 201710348338, 12 pages.
Vaishali et al., "Random and Periodic Sleep Schedules for Target Detection in Sensor Networks", Journal of Computer Science and Technology, May 2008, vol. 23(3) pp. 343-354.

\* cited by examiner

ELECTRONIC VAPOR PROVISION DEVICE

PRIORITY CLAIM

This application is a continuation of application Ser. No. 14/401,511 filed Nov. 14, 2014, which in turn is a National Phase entry of PCT Application No. PCT/EP2013/059954, filed May 14, 2013, which claims priority from GB Patent Application No. 1208352.3, filed May 14, 2012, each of which is hereby fully incorporated herein by reference.

FIELD

The specification relates to electronic vapor provision devices. More particularly, but not exclusively, the specification concerns electronic vapor provision devices in the form of electronic cigarettes.

BACKGROUND

Electronic vapor provision devices are typically cigarette-sized and function by allowing a user to inhale a nicotine vapor from a liquid store by applying a suction force to a mouthpiece. Some electronic vapor provision devices have an airflow sensor that activates when a user applies the suction force and causes a heater coil to heat up and vaporize the liquid. Electronic vapor provision devices include electronic cigarettes.

SUMMARY

In an embodiment there is provided an electronic vapor provision device comprising a body and a vaporizer, wherein the body comprises a power cell and a processor; the vaporizer is releasably connectable to the body; the processor is configured to enter a sleep mode when the vaporizer is connected to the body and the device is inactive for an inactive time; and the processor is configured to leave the sleep mode and enter a usable mode when the vaporizer is disconnected from the body then reconnected to the body.

This has the advantage that once the device has entered a sleep mode, it does not accidentally enter a normal mode. Entering a normal mode requires effort from the user.

The electronic vapor provision device may be an electronic cigarette.

The sleep mode can be a low power mode. Moreover, the sleep mode may be the lowest non-zero power mode of the device.

By remaining in a low power sleep mode the device remains active yet consumes very little power. This provides an efficient use of power and minimizes energy wastage.

The device has a further advantage that it can remain in a low power mode without the additional use of a switch to deactivate and activate.

Furthermore, the electronic vapor provision device can use less power in sleep mode than in usable mode.

Advantageously, the usable mode is a higher power state to enable a more rapid activation once the device is activated by a user.

The electronic vapor provision device may be inactive when not being used as a vapor provision device by a user.

The body may further comprise a capacitor; and the processor can be configured to first charge the capacitor and then detect whether the vaporizer is connected to the body by determining whether the capacitor is discharged.

The body may comprise first and second body connection terminals, and the vaporizer may comprise first and second vaporizer connection terminals. Furthermore, the device may be configured such that when the vaporizer is connected to the body, the first body connection terminal is connected to the first vaporizer connection terminal and the second body connection terminal is connected to the second vaporizer connection terminal.

The capacitor can be connected in parallel with the first and second body connection terminals. The computer can be configured to send out a pulse and the capacitor can be charged for a period of time equal to the width of the pulse. Moreover, the pulse may be a square wave.

In another embodiment there is provided the vaporizer of the electronic vapor provision device of other embodiments.

In another embodiment there is provided the an electronic vapor provision device body, comprising a power cell and a processor, and configured to be releasably connectable to a vaporizer; wherein the processor is configured to enter a sleep mode when the vaporizer is connected to the body and the device is inactive for an inactive time; and the processor is configured to leave the sleep mode and enter a usable mode when the vaporizer is disconnected from the body then reconnected to the body.

In another embodiment there is provided an electronic smoking device comprising a battery assembly and a vaporizer, where the battery assembly comprises a power cell and a computer, the vaporizer is releasably-attachable to the battery assembly and the computer comprises a computer processor, a memory and an input-output means; wherein when the vaporizer is attached to the battery assembly, the computer is configured in use to enter a sleep mode when the device is inactive for a predetermined inactive time.

In another embodiment there is provided a method of triggering a change in the mode of a processor of an electronic vapor provision device from a sleep mode to a usable mode, wherein the electronic vapor provision device comprises a body and a vaporizer; the body comprises a power cell and the processor; and the vaporizer is releasably connectable to the body; the method comprising disconnecting the vaporizer from the body and then reconnecting the vaporizer to the body.

As used herein, the term vapor includes an aerosol and other fluid streams for provision to a user by the electronic vapor provision device.

BRIEF DESCRIPTION OF THE DRAWINGS

For a better understanding of the disclosure, and to show how example embodiments may be carried into effect, reference will now be made to the accompanying drawings in which.

DETAILED DESCRIPTION

Figure 1:
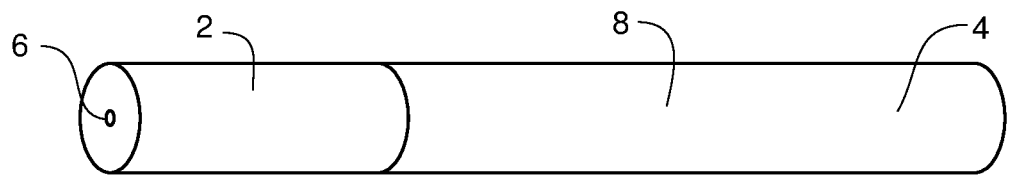
FIG. 1 is a side perspective view of an electronic vapor provision device.
Figure 2:
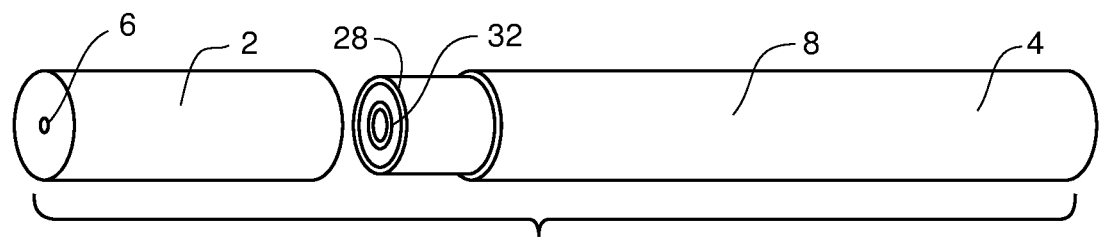
FIG. 2 is an exploded side perspective view of the electronic vapor provision device of FIG. 1.
Figure 3:
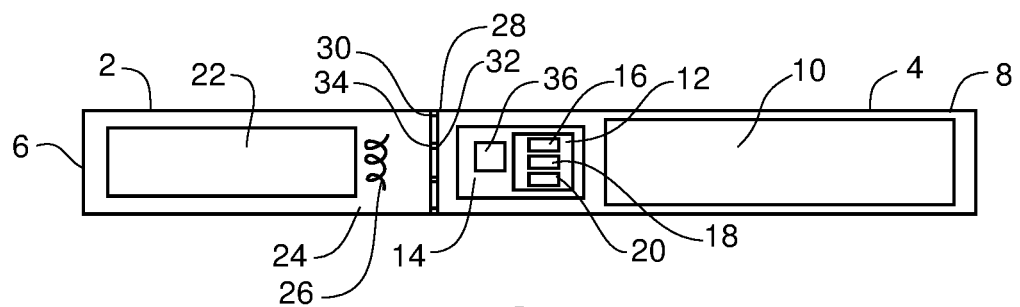
FIG. 3 is a side sectional view through the device of FIG. 1.

Referring to FIGS. 1 to 3 there is shown an electronic vapor provision device, also herein referred to as an electronic smoking device, that comprises a mouthpiece 2 and a body 4. The electronic vapor provision device is shaped like a conventional cigarette, both the mouthpiece 2 and body 4 are cylindrical and are configured to connect to each other coaxially so as to form the conventional cigarette shape. The mouthpiece 2 is connectable to the body 4 at a first end of the mouthpiece 2 and has an air outlet 6 at a second end. The body 2 comprises a battery assembly 8, comprising a power cell 10 and a computer 12 on a circuit board 14, wherein the power cell 10 is connected to the computer 12. The computer 12 comprises a computer processor 16, a memory 18 and input-output arrangement 20. In this example the computer 12 is a microcontroller. The computer 12 is configured to control and interface with the other electrical components of the battery assembly 8, comprising the power cell 10, via the input-output arrangement 20.

The mouthpiece 2 comprises a liquid bottle 22 and a vaporizer 24 having a heater coil 26. For example, the vaporizer 24 is in fluid communication with the liquid bottle 22. The mouthpiece 2 is connectable to the battery assembly 8 by a screw thread, wherein connection of the battery assembly 8 and the mouthpiece 2 connects a first battery assembly terminal 28 to a first vaporizer terminal 30 and a second battery assembly terminal 32 to a second vaporizer terminal 34, forming an electrically conductive contact in both cases. The vaporizer terminals 30 34 are electrically connected in parallel to the heater coil 26 of the vaporizer 24.

The herein described configuration of the computer 12 comprises the computer operating according to a computer program stored in its memory 18 and accessed by its computer processor 16.

The device is configured such that, if the computer determines that the vaporizer 24 is connected to the battery assembly 8, then the computer 12 initially remains in a normal operation mode.

Moreover, to maximize the lifetime of the charge in the power cell 10, the device is configured such that, if the computer 12 determines that the vaporizer 24 is not connected to the battery assembly 8, then the computer 12 enters a low power sleep mode.

Furthermore, to maximize the lifetime of the charge in the power cell 10 while the computer 12 determines that the vaporizer 24 is connected, the computer 12 is configured to detect when the device has been inactive for a predetermined inactive time such as 12 minutes. This inactive time is the time that has elapsed since use of the device by the user. Moreover, in response to detecting that the device has been inactive for the inactive time, the computer 12 is configured to leave normal operational mode and to enter a low power sleep mode. For example, sleep mode may comprise the computer 12 consuming minimal power and performing no processing. A period during which the computer 12 is in sleep mode is herein referred to as sleep time. Furthermore, the device is configured such that, in order to return the device to a normal operational mode, a user is required to disconnect the vaporizer 24 from the battery assembly 8 and then reconnect the vaporizer 24 to the battery assembly 8. This configuration of the device comprises the computer 12 being configured to detect when the vaporizer 24 has been disconnected and then reconnected to the battery assembly 8. Moreover, in response to detection by the computer 12 of disconnection and reconnection of the vaporizer 24, the computer 12 is configured to leave sleep mode and re-enter the normal operation mode.

The computer 12 determining whether the vaporizer 24 is connected to the battery assembly 8 and/or detecting whether the vaporizer 24 has been disconnected and then reconnected may for example comprise the computer 12 periodically checking whether the vaporizer 24 is connected to the battery assembly 8 during both normal operation mode and sleep mode.

For example, after determining that the vaporizer 24 is not attached and entering sleep mode, the computer 12 may then remain in sleep mode for an initial sleep time of two seconds. After the sleep time, the computer 12 wakes and immediately and quickly checks again for a vaporizer connection. Again, if the vaporizer 24 is not connected the computer 12 goes into sleep mode for another two seconds. The time that the computer 12 is awake is extremely short compared to the sleep time so the circuit remains predominantly in a low power mode, thus conserving power. During the sleep time no checks are made to determine whether the vaporizer 24 is attached however a user may take several seconds to assembly the device, connecting the vaporizer 24 and the battery assembly 8, so the vaporizer 24 connection may be easily established by the computer 12 before use of the device by a user.

Furthermore, after determining that the vaporizer 24 is connected and that the device has been inactive in this connected state for the inactive time and then entering sleep mode, the computer 12 may then remain in sleep mode for an initial sleep time of two seconds. After the sleep time, the computer 12 wakes and immediately and quickly checks again for a vaporizer connection. Again, if the vaporizer is still connected the computer 12 goes into sleep mode for another two seconds. The time that the computer 12 is awake is extremely short compared to the sleep time so the circuit remains predominantly in a low power mode, thus conserving power. During the sleep time no checks are made to determine whether the vaporizer 24 is attached. However a user may take several seconds to disconnect the vaporizer 24 and several seconds to then reconnect the vaporizer 24, so the computer 12 may easily detect and log the disconnection and subsequent reconnection. In this way the computer 12 is able to detect the disconnection and subsequent reconnection of the vaporizer 24 by a user and to respond accordingly by leaving sleep mode and entering normal operation mode.

The waking of the computer 12 may for example comprise the computer 12 entering a waking mode distinct from the sleep mode and the normal operation mode.

The computer 12 checking whether the vaporizer 24 is connected to the battery assembly 8 may for example comprise the computer 12 sending an electrical pulse to the battery assembly terminals 28, 32. For example, the computer 12 may control the power cell 10 so as to supply a pulse of current to the first battery assembly terminal 28 and may measure the current reaching the second the battery assembly terminal 32, for example using a digital multimeter of the battery assembly 8. The digital multimeter is referenced 44 in the circuit diagram of FIG. 8. Furthermore, if the vaporizer 24 is connected, the digital multimeter reads a current reaching the second battery assembly terminal 32 via the vaporizer 24 and provides information to the computer 12 indicating this.

The battery assembly 8 of the electronic cigarettes described herein further comprises an air pressure sensor 36, wherein the air pressure sensor is powered by the power cell 10 and controlled by the computer 12. Once the vaporizer is connected to the battery assembly 8, and while the device is still in the normal operation mode resulting from the processors detection of this connection, in order to use the device the user must suck on the mouthpiece 2. The electronic cigarette is configured such that the user sucking on the mouthpiece 2 causes a drop in air pressure at the air pressure sensor 36. The computer 12 therefore receives information from the air pressure sensor 36 indicating that a user is sucking on the device. In response to this information, the computer 12 controls the power cell 10 to power the vaporizer 24. For example, the computer may control the power cell 10 to power the vaporizer 24 via the respective first and second terminals of both the battery assembly and the vaporizer. This causes the vaporization of liquid communicated to the vaporizer 24 from the liquid bottle 22. Consequently, use of the device by a user comprises the user sucking on the device and the detection of this user interaction by the device so as to trigger the vaporization of the liquid contained in the device. The provided vapor then passes to the user. The vapor provision device is configured such that a user can only use the device, by sucking on the mouthpiece 2, when the computer is in the normal operation mode. The normal operation mode can therefore be described as a usable mode.

Figure 4:
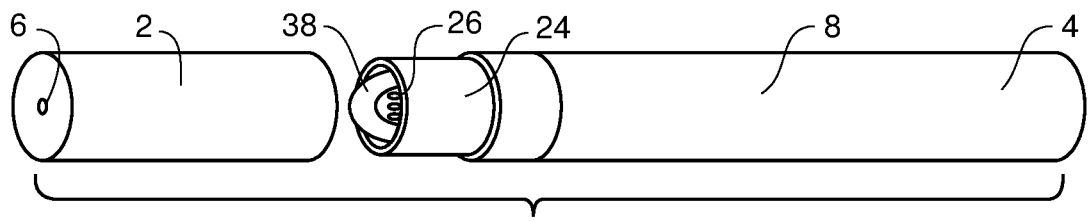
FIG. 4 is a side perspective view of an electronic vapor provision device with separated mouthpiece and body.
Figure 5:
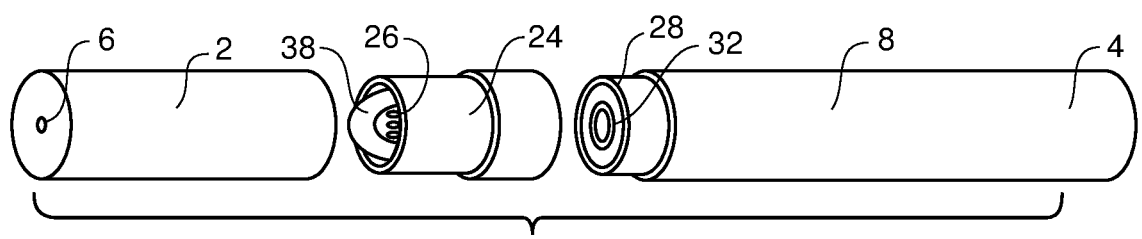
FIG. 5 is a side perspective view of an electronic vapor provision device with separated mouthpiece, vaporizer and battery assembly.
Figure 6:
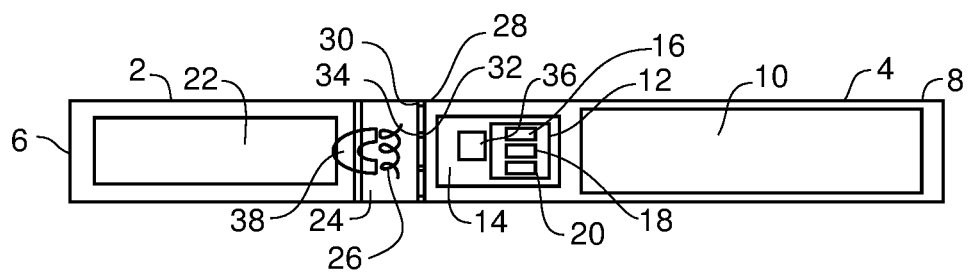
FIG. 6 is a side sectional view through the electronic vapor provision device of FIG. 4 with connected mouthpiece and body.

FIGS. 4 to 6 show another example of an electronic vapor provision device. This device is similar to that shown in FIGS. 1 to 3. However in this example the vaporizer 24 does not form part of the mouthpiece 2. The mouthpiece 2 contains a liquid bottle 22 and is attachable to the vaporizer 24. The vaporizer 24 has a heater coil 26 and additionally a wick 38. For example the wick 38 may be a mesh wick. The mouthpiece 2 and the vaporizer 24 are configured to connect to each other such that the wick 38 acts to communicate liquid from the liquid container 22 onto the vaporizer 24. The configuration of the device involving the conservation of power based on interaction between the vaporizer 24 and the battery assembly 8 involving the disconnection and reconnection of the vaporizer is as described above.

Figure 7:
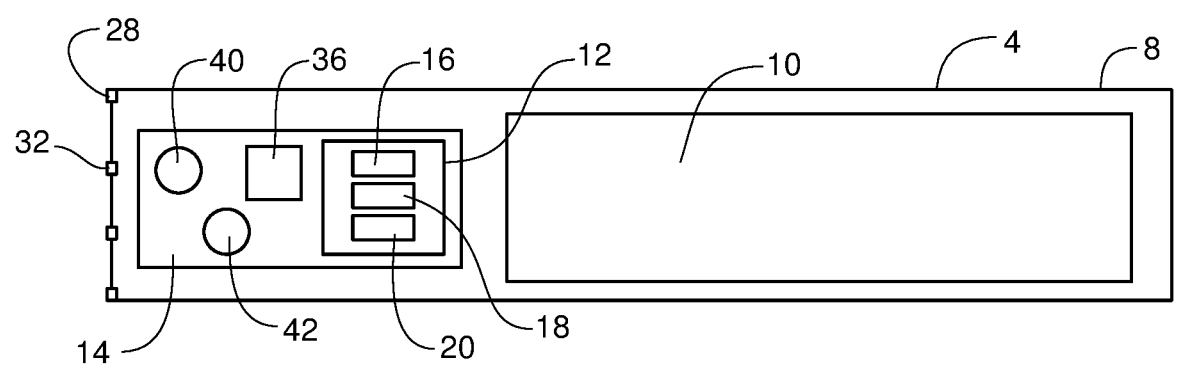
FIG. 7 is a side sectional view of a battery assembly having a capacitor.
Figure 8:
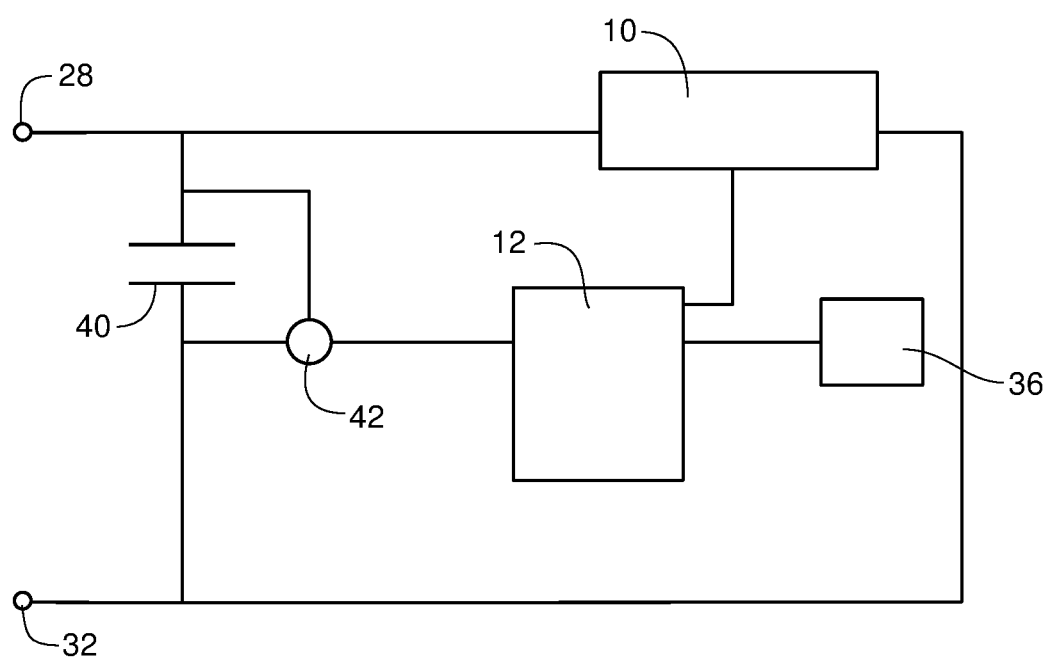
FIG. 8 is a circuit diagram for the battery assembly of FIG. 7.

A further example of how, in the cigarettes of FIGS. 1 to 6, connection of the vaporizer 24 to the body may be detected by the computer 12 is now described with reference to FIGS. 7 and 8. With respect to FIGS. 7 and 8, the battery assembly 8 of the electronic vapor provision device is similar to that shown in FIG. 1 to FIG. 6, additionally comprising a capacitor 40 and a digital multimeter 42. The capacitor 38 is arranged in a circuit such that it is in parallel to the battery assembly terminals and to the power cell 10. The digital multimeter 42 of the battery assembly 8 is wired in a switched parallel circuit to the capacitor 40. To test whether the vaporizer 24 is connected to the battery assembly 8, the computer 12 first controls the power cell to charge the capacitor 40, then waits a short time and checks the charge of the capacitor 40. The computer 12 checks the charge of the capacitor 40 by triggering the completion of the switched digital multimeter circuit and then receives information from the multimeter 42 indicating a voltage across the capacitor 40 resulting from the charge of the capacitor 40. If the vaporizer 24 is connected, the resistance of the vaporizer 24 causes the capacitor 40 to discharge quickly so the computer 12 measures at least a substantially fully discharged capacitor 40. If the vaporizer 24 is not connected the capacitor 40 is not substantially fully discharged when checked by the computer 12.

With regard to the embodiments described herein, the following alternatives and variations will now be described.

The electronic vapor provision devices described may be electronic cigarettes. However, the device is not restricted to being cigarette shaped.

The sleep time may be substantially 2 seconds. However, the sleep time is not restricted to 2 seconds and other suitable values could be used. Moreover, the time between entering sleep modes can be significantly less than the sleep time.

The computer processor 16 can be a microprocessor. Moreover, the computer 12 may comprise a microcontroller. Furthermore, a computer such as a microcontroller could utilize a watchdog timer to implement the sleep time wait in the low power mode. Using a microcontroller has space saving advantages since the entire computer is located on a single chip and therefore the size of the device is minimized. Fewer components to assemble also provides reduced manufacturing times are costs. The computer is not restricted being a microcontroller and could be fabricated from separate processor, memory and input-output components.

The vaporizers 24 described are examples only.

Moreover, the sleep mode may be the lowest non-zero power mode of the device.

Although an air pressure sensor 36 is described, other configurations may be employed to detect when a user is attempting to use the device. For example, an airflow sensor may be used and the device may be configured such that sucking on the mouthpiece 2 by a user causes a flow of air past the airflow sensor.

Although a liquid bottle 22 is described, other types of liquid storage may be used. For example the device may comprise foam partially saturated in liquid for vaporization.

Although a digital multimeter 42 is described as being used by the computer 12 to determine the level of charge of the capacitor 40, other suitable configurations may be employed for this purpose. For example, a digital voltmeter may instead be used.

The electronic vapor provision devices are described as being configured such that the computer 12 can determine when the vaporizer 24 is connected to the battery assembly 8 of the body 4. This configuration of the electronic vapor provision device may be described as the device comprising a sensor arrangement configured to detect when the vaporizer is connected and to provide information to the processor accordingly. For example, with regard to the device of FIGS. 7 and 8, the first and second battery assembly terminals 28 32, the capacitor 40 and the digital multimeter 42 may together be considered as a sensor arrangement of the device. In this sense, the sensor arrangement may take other forms to that described. For example, the sensor arrangement may comprise only one sensor, for instance a pressure sensor configured to detect a mechanical pressure resulting from connection of the vaporizer 24 to the body 4.

The various embodiments described above facilitate a number of improvements.

The described configuration of the electronic vapor provision device is such that in the case of the vaporizer 24 being connected and the device entering the sleep mode due to the device being inactive for the inactive time, the device can not then accidentally enter a normal mode. Moreover, a user must be aware of the requirement to disconnect and then reconnect the vaporizer 24 and must carry this procedure out in order to trigger the device to enter the usable, normal operation mode. Entering a normal mode requires effort from the user. This facilitates the advantage of increased safety and control of use of the device.

Described operational modes and configurations of the computer may be operational modes and configurations of the processor.

Although examples have been shown and described, it will be appreciated by those skilled in the art that various changes and modifications might be made without departing from the scope of the invention.

In order to address various issues and advance the art, the entirety of this disclosure shows by way of illustration various embodiments in which the claimed invention(s) may be practiced and provide for superior electronic vapor provision devices. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. An electronic vapor provision device comprising:
a battery assembly; and
a vaporizer,
wherein the battery assembly comprises a power cell and a computer, the vaporizer is releasably-attachable to the battery assembly and the computer comprises a computer processor, a memory and an input-output means, and wherein the computer is configured to determine when the vaporizer is attached to the battery assembly and, when the computer determines the vaporizer is attached to the battery assembly, the computer is configured in use to remain in a normal operation mode and to enter a sleep mode when the device is inactive for a predetermined inactive time, and when the computer determines the vaporizer is not attached to the battery assembly the computer is configured in use to enter the sleep mode, and
wherein the computer is configured to periodically check whether the vaporizer is connected to the battery assembly during both the normal operation mode and the sleep mode.

2. The electronic vapor provision device of claim 1, wherein the electronic vapor provision device is an electronic cigarette.

3. The electronic vapor provision device of claim 1, wherein the sleep mode is a low power mode.

4. The electronic vapor provision device of claim 1, wherein the sleep mode is the lowest non-zero power mode of the device.

5. The electronic vapor provision device of claim 1, wherein the electronic vapor provision device uses less power in sleep mode than in usable mode.

6. The electronic vapor provision device of claim 1, wherein the electronic vapor provision device is inactive when not being used as a vapor provision device by a user.

7. The electronic vapor provision device of claim 1, wherein:
the body comprises first and second body connection terminals, and the vaporizer comprises first and second vaporizer connection terminals; and
the device is configured such that when the vaporizer is connected to the body, the first body connection terminal is connected to the first vaporizer connection terminal and the second body connection terminal is connected to the second vaporizer connection terminal.

8. The electronic vapor provision device of claim 1, wherein:
the body further comprises a capacitor; and
the processor is configured to first charge the capacitor and then detect whether the vaporizer is connected to the body by determining whether the capacitor is discharged.

9. The electronic vapor provision device of claim 8, wherein the capacitor is connected in parallel with the first and second body connection terminals.

10. The electronic vapor provision device of claim 8, wherein the computer is configured to send out a pulse and the capacitor is charged for a period of time equal to the width of the pulse.

11. The electronic vapor provision device of claim 10, wherein the pulse is a square wave.

12. The electronic vapor provision device of claim 1, wherein the vaporizer further comprises a mesh wick.

13. An electronic vapor provision device body, comprising:
a power cell and a processor, and configured to be releasably connectable to a vaporizer,
wherein the processor is configured to determine when the vaporizer is attached to the vapor provision device body and, wherein the processor is configured to remain in a normal operation mode when it is determined the vaporizer is attached to the vapor provision device body, to enter a sleep mode when the processor determines the vaporizer is connected to the body and the device is inactive for a predetermined inactive time, and to enter the sleep mode when it is determined, in use, the vaporizer is not attached to the vapor provision device body, and
wherein the processor is configured to periodically check whether the vaporizer is connected to the vapor provision device body during both the normal operation mode and the sleep mode.

* * * * *